United States Patent [19]

Chodorow et al.

[11] 4,275,736

[45] Jun. 30, 1981

[54] RETENTION SUTURE BRIDGE

[75] Inventors: Ingram S. Chodorow, Upper Saddle River, N.J.; J. David Dainow, New York, N.Y.

[73] Assignee: Technalytics, Inc., Upper Saddle River, N.J.

[21] Appl. No.: 263

[22] Filed: Jan. 2, 1979

[51] Int. Cl.³ ............................................ A61B 17/04
[52] U.S. Cl. .................................................... 128/335
[58] Field of Search ........................... 128/334 R, 335

[56] References Cited

U.S. PATENT DOCUMENTS

| | | | |
|---|---|---|---|
| 1,852,098 | 4/1932 | Anderson | 128/335 |
| 3,014,483 | 12/1961 | McCarthy | 128/334 R |
| 3,473,528 | 10/1969 | Mishkin et al. | 128/335 X |
| 3,695,271 | 10/1972 | Chodorow | 128/335 |

Primary Examiner—Dalton L. Truluck
Attorney, Agent, or Firm—J. David Dainow

[57] ABSTRACT

This invention is a retention suture bridge device for positioning and securing the exposed portion of a retention suture above and out of contact with an incision closure while the retention suture remains tied. This new device is formed of an arch part with end parts thereof aligned along a longitudinal axis, a series of holes along the arch through which the ends of a retention suture may be extended, and a generally round foot part secured to each end part and pivotal on the end part about the longitudinal axis.

18 Claims, 5 Drawing Figures

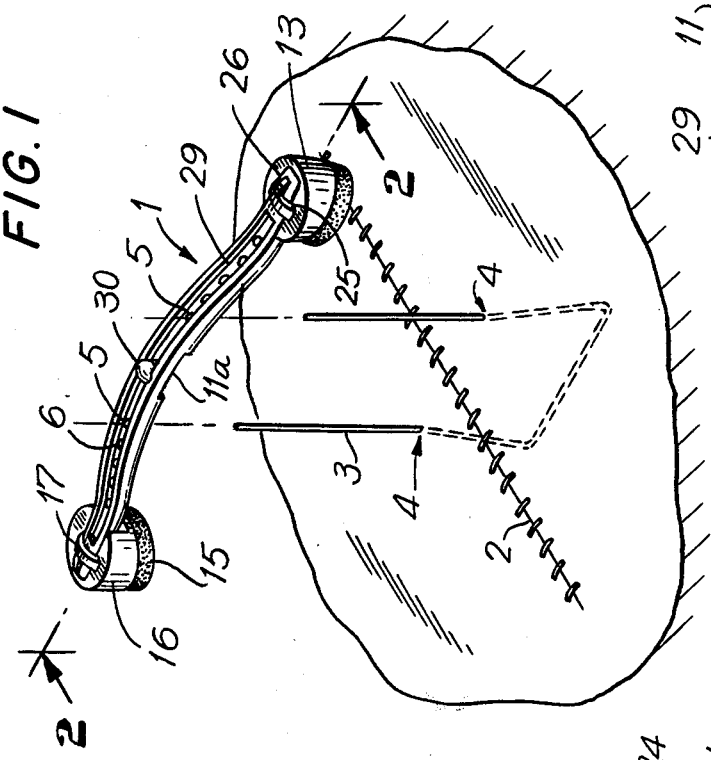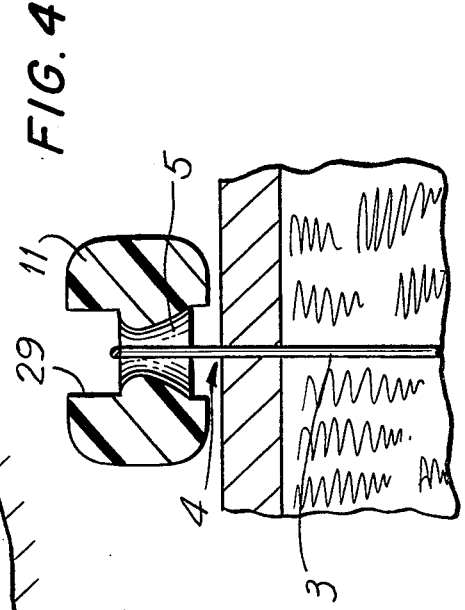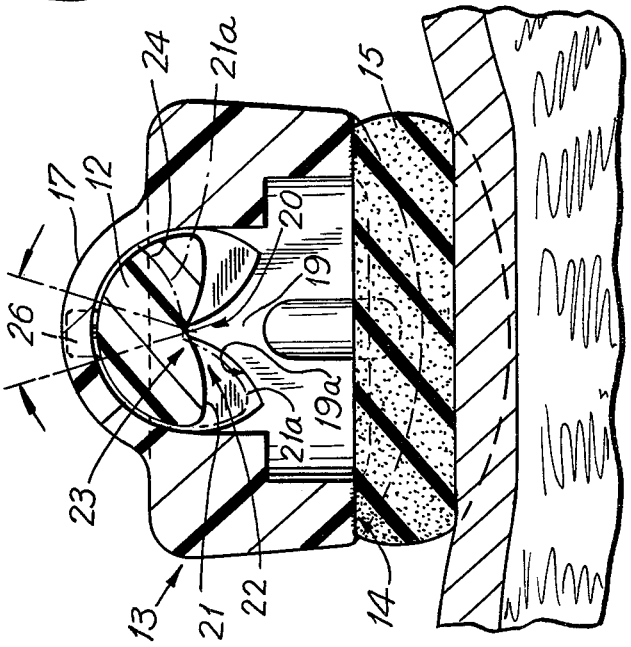

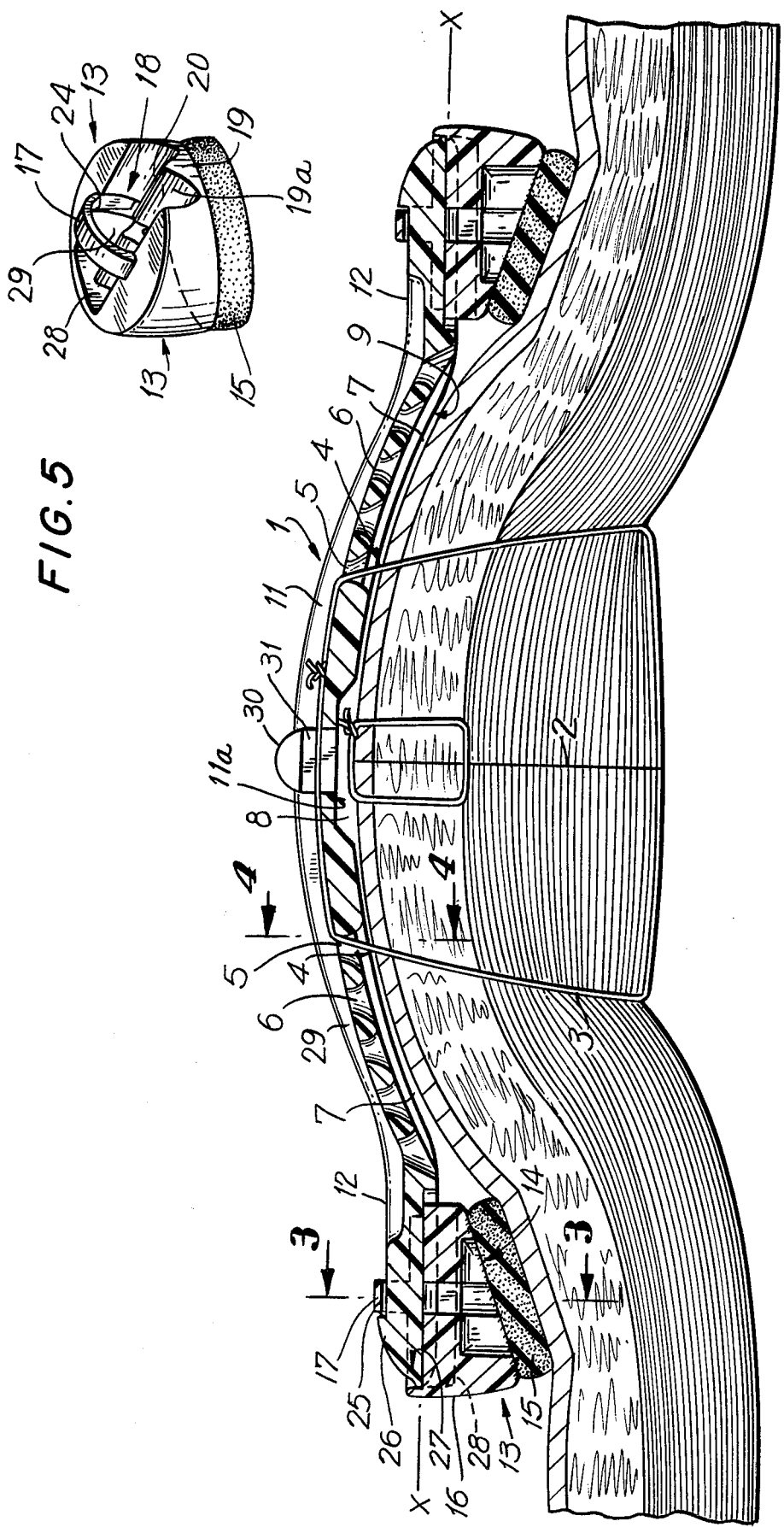

RETENTION SUTURE BRIDGE

BACKGROUND OF THE INVENTION

In large abdominal incisions, successful closure often requires in addition to skin sutures at the exposed outer layers, the use of transverse tension sutures, usually designated stay or retention sutures, which are relatively large loops that extend down through both sides of and under an incision, and extend over and are tied across the closure. Such retention sutures pass through numerous layers of tissue, such as fascia, fat and muscle, and are tied tightly to help position and join each layer to its appropriate counterpart and to hold these severed tissues in proper juxtaposition. After closure the incision area usually has certain swelling owing to edema caused by the physical and chemical trauma of surgery, thus causing tightening of the sutures. Internal or external body movement or muscular strain is likely to place additional tension in the sutures.

In the typical cases where the sutures are in contact with the skin under them, the strain and swelling results in increased suture tension, with the suture impressing itself deeply into the skin causing redness of erythema, infection which slows or otherwise impairs healing, necrosis of tissue cells and/or increased scarring and cross-hatching, sometimes called railroad scarring.

Various techniques and devices have been used in attempts to obviate these problems. Initial attempts involved loose tying of sutures to allow for swelling, but this left the incision not securely closed. According to one current and widely used technique a section of rubber catheter tubing is cut to a length generally the same as the distance between the exit points of the suture from the skin on either side of an incision. One of the two exposed portions of each suture is threaded through the bore of a section of catheter and tied to the other portion. This technique of using catheter sections has the disadvantage of failing to maintain lateral fixation of the portions of the retention suture at the exit points, because the flexible tubing bends or buckles; also with such catheter sections the above-mentioned problem of pressure necrosis remains, due to pressure contact of the tube along its length against the skin and particularly at the exit points.

Rigid tubes of fixed and varying length have been used; however, along their length they also bear upon the skin surface, causing cross-hatch scarring of considerable extent. Flat pieces of wood, metal and plastic of fixed length with notches in opposite ends have also been employed, but these have the same disadvantages as rigid tubing. Further description of prior art as generally relates to retention sutures may be found in U.S. Pat. No. 3,695,271, which discloses a retention suture bridge comprising a resilient, single piece arch whose ends are formed as continguous and fixed feet. This device has been used to support the exposed portion of the retention suture off and above the the wound; however in use an unexpected problem occurred, namely tipping of the arch from its initially upright orientation. This was due to a variety of causes including, excessive tension in the suture either when tied or after swelling of the incision area, change of stomach contours when a patient sat up or turned, or swelling of the tissue under one side of one or both feet. Any such tipping of the arch necessarily and simultaneously tipped the bridge feet; also tipping of one foot simultaneously tipped the other foot. Where a foot tipped, the tipped arch could then be lying against the incision and thus no longer function exactly as intended; where the arch tipped the side edges of the connected foot could press into adjacent skin leading to bruising and discomfort. The present invention is concerned particularly with an improvement over the device disclosed and claimed in this U.S. Pat. No. 3,695,271.

The objectives of the present invention extend considerably beyond those in the above-cited patent, and are now accomplished with a new and significantly different retention suture bridge device. The various objectives include provision of a device for maintaining the exposed portion of a retention suture above and out of contact with the incision closure area, while the device itself has minimal or no pressure contact with this area. It is a further objective to maintain lateral fixation of the suture exit points and thereby to stabilize the area of the joined tissues and prevent separation of the joined tissues. The new device should readily accommodate retention sutures having a variety of distances between suture and exit points, without irritation of the skin at these exit points.

An additional objective is to provide a device which conforms well to the contours of a typical abdomen where retention sutures are most commonly used, and which remains secure and properly oriented relative to the engaged retention suture and the incision closure area, even when the patient moves or bends or when the skin of the incision area under a foot part of the device or under the arch becomes swollen or otherwise distorted. More specifically the new device overcomes the problems where movement by a patient or swelling of the incision area tips the device about its longitudinal axis, causing the side of the arch portion or of a foot portion to contact and/or press against adjacent skin, or to pull the tied retention suture more tightly than should be experienced. The new invention achieves substantially all of the above-discussed objectives with a structure that is simple yet reliable, as described in the following paragraphs.

SUMMARY OF THE INVENTION

This invention is a new retention suture bridge device for engaging and securing the exposed portion of a retention suture above and out of contact with the incision closure area. In use each particular suture has exposed end parts extending out of the exit points of the skin, which exit points define between them a specific distance when the wound is closed. The surgeon merely extends these suture ends upward into two holes in the arch, which holes are spaced apart a distance generally corresponding to the distance between the exit holes. It is preferable that surgeon select two holes spaced apart a distance less than the distance between the suture exit points, so that the suture ends, upon entering the arch holes will be slightly converging, and thus will provide a lateral force vector in the suture which aids in holding the wound tightly closed until healing is achieved. The arch has a plurality of holes along its length to accommodate most normal variations in pitch or the distance between exit points of retention suture end parts. Instead of holes through the arch a variety of other suture-engaging means are possible; holes were selected for their simplicity and reliability.

The new device has movable feet secured to opposite end parts of the arch; the feet are pivotable about a longitudinal axis extending through these end parts, each foot being pivotable independently of the other foot. Accordingly, one foot could pivot clockwise while the other foot pivots counter-clockwise, or clockwise, or remained unpivoted. Conversely, one or both feet may remain oriented in an upright manner while the arch pivots clockwise or counter-clockwise about the axis through the two feet. With this extensive freedom of rotational movement the new device can react to, and accommodate most of the predictable and unpredictable movements of a patient and/or swelling anywhere in the incision closure area. Accommodation of the device in this sense means that the arch can remain relatively upright as it appeared when originally attached to a patient lying flat, regardless of the above-described movement or swelling of the patient.

This new device provides an important advance over prior art devices having feet which are fixedly attached to the arch or which pivot about axes transverse of the arch, because all such prior art devices tend to lose their original orientation and stability when there is a change in height or contour of the skin surface under either foot, a substantial change of tension of the suture tied to the arch, or severe movement or strain by the patient. As mentioned above, pivoting of the feet about transverse axes will not alleviate or avoid the problems to which this present invention is addressed.

The particular structure for permitting the feet to pivot about a longitudinal axis may take many forms; however, in preferred embodiments the following requirements must be satisfied. The feet must pivot freely, yet be securely prevented from becoming separated from the arch, since separation would be intolerable during use. The movable feet must not interfere with the basic function of the arch in its relation to a retention suture bridge. The cost and ease of manufacture and assembly must be reasonable; the device must be easy to understand and use by surgeon; and the device must not create any new problems or discomforts while eliminating old ones. Preferred embodiments of this invention are illustrated in the attached drawings and described in the following paragraphs.

DESCRIPTION OF THE DRAWINGS AND THE PREFERRED EMBODIMENTS

The preferred embodiment of this new invention is illustrated in the accompanying drawings, summarized as follows.

FIG. 1 is a perspective view of the new retention suture bridge assembly;

FIG. 2 is a longitudinal sectional view taken along line 2—2 of FIG. 1, of the new retention suture bridge in use with a retention suture tied about a wound;

FIG. 3, is a cross-sectional view of the left end of the bridge and foot taken along line 3—3 of FIG. 2;

FIG. 4 is a cross-sectional view of the bridge taken along line 4—4 of FIG. 2; and FIG. 5 is a perspective view of the left foot.

DETAILED DESCRIPTION OF THE PREFERRED EMBODIMENTS

The new retention suture bridge is applied to a patient in a generally similar manner as the prior art device of the cited prior art patent, however thereafter the operation of this device in relation to the wound is substantially different due to the new structure and new theory of operation. FIGS. 1 and 2 illustrate the new bridge 1 situated above a wound closure 2 with a retention suture 3 sewn about the wound and over and tied atop the bridge. The ends of the suture 3 extend out of exit points 4 on either side of the incision 2 and then upward and slightly converging into holes 5 which are spaced apart a distance which corresponds generally with the distance between exit points 4. Obviously holes 6 could be used if the pitch of the retention suture, i.e., the space between exit points happened to be greater. Spaces 7 and 8 between the bridge's lower surface 9 and the closure area's upper surface, will vary with many factors, but at all times there will be greatly reduced or sometimes no pressure contact between these surfaces, as compared with the prior art devices described in the Background of the Invention. To insure this minimal contact the central arch part 11 of the bridge is undercut upward providing recess 11a, and the radius of curvature of the bottom surface of the arch is approximately 3.7 inches along an arch length of about 3 inches to conform generally to a typical abdomen, as shown in FIG. 2.

Now, consider the whole bridge assembly of FIG. 2, wherein the opposite ends 12 of the arch 11 are aligned along the single pivot axis X—X. The feet 13 pivot on this axis independently of each other, depending upon the contours of the patient's abdomen where they are situated, as will be described in detail in later paragraphs.

The feet 13, as shown in FIGS. 1–3 and 5, are pivotally connected to ends 12 of the arch in the following manner. Each foot 13 has a base surface 14 covered by a foam pad 15, sides 16, and a top strap 17. Beneath the strap is an aperture 18 which is generally circular about a central axis which coincides with axis X—X of the arch feet when these components are assembled. A pivot pedestal or blade 19 extends upward from the bottom of aperture 18, with the top 20 of blade 19 situated essentially at the center of the aperture, and therefore along axis X—X.

It can be seen that the bottom portion 21 of end 12 of the arch 10, defines a smooth inverted V-shaped recess 22, with an apex 23 which pivotally engages the top 20 of the blade 19. FIG. 3 shows that end 12 is pivotable within the strap 17, and pivot blade 19 of the foot. The solid line 21 represents the bottom of end 12 with the arch in an upright orientation. The dotted line 21a represents the same bottom of end 12 when the arch has pivoted counter-clockwise until surface 21a is about to be stopped by curved surface 19a of the pivot pedestal 19. Obviously the degrees of rotation of the arch relative to the feet may be varied by extending or cutting away the surfaces 21,21a and/or 19a.

Strap 17 has an underside 24 which functions partly as a bearing surface and partly as radial restraining means. The strap also has a side edge 25 as illustrated in FIGS. 1 and 2 which functions primarily as an axial restraining and locking means. The mating element for strap 17 is a finger 26 which may be resilient in one embodiment, or fixed in another embodiment. At the time of assembly each foot part 13 is aligned with one end of the arch until an end part 12 is inserted into aperture 18, the top surface of end 12 engages the underside 24 of the strap, while the top 20 of blade 19 engages pivot recess 23 of the end 12. In the resilient finger embodiment the strap is moved axially until it covers and deflects finger 26 downward into its adjacent recess, and the strap edge 25 passes the end of finger 26; immediately finger 26 springs upward and acts as a stop to prevent the strap 17 and the associated foot 13 from coming off this end of the arch, while still permitting the foot to freely pivot within certain limits of rotation. The spring 26 is designed to be relatively stiff and thus to require a very substantial effort to depress and release the strap and foot from attachment to the arch. A variety of other means are also feasible for permanently or releasably locking the foot onto the arch; the end part 12 of the arch may have a continuous surface that is smoothly insertable through the strap 17, with a separate collar or transverse pin (not shown) secured on the portion of the end part 12 extending through and beyond the strap. Another variation of fastening means would provide for finger 26 to be an essentially rigid projection from end part 12 of the arch; strap 17 would be somewhat flexible or stretchable, so that it could be deflected to permit insertion of end 12 and finger 26 through the opening, but in operation would maintain suitable curvature and dimensions to preclude the foot from being separated from the arch.

As shown in FIG. 3 the foot 12 and arch are relatively pivotable, by the engagement of surface 21 with the top part 20 of pivot blade 19 of the foot. The similarity in principal might be noted of this pivot-coupling to that used with precision scales or balances; in both frictional contact is minimized as much as is feasibly possible, while still providing adequate strength of the parts to reliably support the loads involved.

When a retention suture bridge is used and a retention suture is threaded through apertures 5-6, etc., and is tightly tied, the ends 12 will bear downward hard against the pivotable feet; this downward force will increase friction and tend to reduce their freely pivotable relationship when the patient moves or during swelling or other changes in the wound configuration. To insure that these parts will remain freely pivotable regardless of the loading, the pivot blade and recess structure, or other anti-friction structure is preferable. Obviously one may choose other rotational coupling means which do not include this anti-friction feature.

An additional feature to minimize friction in this pivot coupling is a thrust bearing formed by tit 27 at the tip extremety of arch end 12 which bears against end surface 28 in recess 29 of foot 12. The tit 27 has an extremely small, axially-facing surface area for contact with end surface 28, so that any axial thrust and movement of the arch relative to the feet in either direction will produce only minimal friction. In a further embodiment of this thrust bearing the tit 27 may include a central aperture that receives and is guided by a small projection (not shown) extending from end surface 28 in the axial direction of the arch. If desired this thrust bearing in combination with the strap and finger 26 or other coupling, may allow for axial play of the arch relative to the feet.

To facilitate threading and securing a retention suture onto the new bridge there are the following additional structural features. As shown in FIGS. 2 and 4 the bottom of each aperture 5-6, etc. is wider than the top, and preferably the bottom flares outward providing a funnel effect for insertion of a suture. Along the top surface of the arch 11 is axial groove 29 which guides and encloses the tied suture below the top surface of the arch. This groove also protects the tied suture from being snagged, pulled or cut by a foreign object. The turret 30 as shown in FIGS. 1 and 2 has space or tunnel 31 beneath it through which the tied suture extends; this turret also serves as a suture tying post for those surgeons who want it.

Finally, to further enhance the comfort of this new bridge when in use, a foam rubber pad 15 is adhered to the bottom surface 14 of each foot 13. The foam composition allows air circulation through it which helps keep the skin surface under the foot relatively dry; also the cavity and aperture through the foot, due to the injection molding technique, further enhance breathing of the skin beneath the foot.

What is claimed is:

1. A bridge device for use with a retention suture looped about the juxtaposed layers of a wound or incision to be closed, the suture thus being partially below the surface of the juxtaposed layers with two exposed end parts of the suture extending out of and above a pair of exit points in the outer layer of skin, these exit points being located on both sides of the incision and defining between them a line generally perpendicular to the incision, the bridge device comprising:
   (a) an arch having a central part and opposite end parts, the central part having top and bottom surfaces and length defined between said end parts,
   (b) a plurality of suture-engaging means spaced apart along said central part in the lengthwise direction,
   (c) first and second foot parts, and
   (d) pivot means pivotally coupling each of said first and second foot parts to one of said end parts, each pivot means permitting pivotal movement of one foot independent of the other foot about an axis extending in the lengthwise direction relative to said central part.

2. A bridge according to claim 1 wherein each foot part includes a pivot aperture which is at least partially round in a plane transverse of the pivot axis therethrough, and each end part is insertable into and pivotable in said aperture.

3. A bridge according to claim 2 wherein each foot comprises a base part for contacting the outer layer of skin, an upper part, and a strap extending from and defining with said upper part said pivot aperture.

4. A bridge according to claim 1 wherein said pivot means permits coupling of each foot part with an end part, but when coupled, essentially precludes said coupled parts from being decoupled.

5. A bridge according to claim 4 wherein each of said end parts and the associated foot part comprise a pair of relatively pivotable members, and said connection means comprises a resilient element on one member of said pair of pivotable members and a connecting element on the other member of said pair, said resilient element being deflectable for releasably engaging said connecting element for coupling and decoupling said pair of relatively pivotable members.

6. A bridge according to claim 1 wherein said central part top and bottom surfaces define convex and concave surfaces respectively, which have a radius of curvature of about 3.7 inches.

7. A bridge according to claim 1 wherein said suture engaging means comprises a row of axially-spaced apertures in said central part, each aperture extending between and through said top and bottom surfaces thereof.

8. A bridge device according to claim 1 wherein said central part defines a smooth concave curve along the bottom surface thereof, and within said concave curve is a similarly oriented concave recess in the vicinity of the center of the central part.

9. A bridge device according to claim 1 further comprising means for varying the tension in the suture engaged by said suture-engaging means.

10. A bridge device according to claim 1 wherein each of said foot parts has a bottom surface oriented generally similarly as the bottom surface of said central part, said bridge further comprising a resilient pad secured to and generally covering said bottom surface of each foot part.

11. A bridge device according to claim 1 wherein said top surface of said central part defines a trough.

12. A bridge device according to claim 11 wherein said top surface of said central part further defines a turret situated above said trough and intermediate said end parts, with a tunnel being defined between said turret and trough.

13. A bridge device as in claim 1 wherein
each of said first and second foot parts pivots about a common axis.

14. A bridge device for use with a retention suture looped about the juxtaposed layers of a wound or incision to be closed, the suture thus being partially below the surface of the juxtaposed layers with two exposed end parts of the suture extending out of and above a pair of exit points in the outer layer of skin, these exit points being located on both sides of the incision and defining between them a line generally perpendicular to the incision, the bridge device comprising:
(a) an arch having a central part and opposite end parts, the end parts being aligned along a central axis therethrough and the central part having top and bottom surfaces and length defined between said end parts,
(b) a plurality of suture-engaging means spaced apart along said central part in the lengthwise direction,
(c) first and second foot parts, and
(d) pivot means for pivotally coupling each of said first and second foot parts to one of said end parts and permitting pivotal movement of each foot independent of the other foot about said central axis, each of said end parts and the foot part associated therewith comprising a pair of relatively pivotal members, and said pivot means comprising a blade extending from a first of said members with an edge of the blade being generally coaxial with said pivot axis, and a recess in the second of said members, the recess having walls which define a generally V-shape in cross-section, said blade being situated with said edge thereof engaging the apex of said recess.

15. A bridge according to claim 14 wherein said first and second members comprise a foot part and an end part respectively.

16. A bridge according to claim 14 wherein said pivot means permits a degree of rotational freedom defined by the amount of divergence of the V, the curvatures of the walls defining the recess, and the shape of the blade.

17. A bridge device for use with a retention suture looped about the juxtaposed layers of a wound or incision to be closed, the suture thus being partially below the surface of the juxtaposed layers with two exposed end parts of the suture extending out of and above a pair of exit points in the outer layer of skin, these exit points being located on both sides of the incision and defining between them a line generally perpendicular to the incision, the bridge device comprising:
(a) an arch having a central part and opposite end parts, the end parts being aligned along a central axis therethrough and the central part having top and bottom surfaces and length defined between said end parts,
(b) a plurality of suture-engaging means spaced apart along said central part in the lengthwise direction,
(c) first and second foot parts, and
(d) pivot means for pivotally coupling each of said first and second foot parts to one of said end parts and permitting pivotal movement of each foot independent of the other foot about said central axis said end part having a terminal end with an axially extending tit of relatively small diameter, and each of said foot parts having and end wall engaged by said tit, this engagement defining a very small area of contact for minimizing frictional resistance therebetween.

18. A bridge device for use with a retention suture looped about the juxtaposed layers of a wound or incision to be closed, the suture thus being partially below the surface of the juxtaposed layers with two exposed end parts of the suture extending out of and above a pair of exit points in the outer layer of skin, these exit points being located on both sides of the incision and defining between them a line generally perpendicular to the incision, the bridge device comprising:
(a) an arch having a central part and opposite end parts, the end parts being aligned along a central axis therethrough and the central part having top and bottom surfaces and length defined between said end parts,
(b) a plurality of suture-engaging means spaced apart along said central part in the lengthwise direction,
(c) first and second foot parts, and
(d) pivot means for pivotally coupling each of said first and second foot parts to one of said end parts and permitting pivotal movement of each foot independent of the other foot about said central axis, each foot part comprising a pivot aperture which is at least partially round in a plane transverse of the pivot axis therethrough, and each end part being insertable into and pivotable in said aperture, each foot part further comprising a base part for contacting the outer layer of skin, an upper part, and a strap extending from and defining with said upper part said pivot aperture, and each of said end parts further comprising a proximal portion of first diameter adjacent the central part and a distal end having second diameter greater than the first diameter, and said pivotal aperture defined partially by said strap having a third diameter less than said second diameter and slightly greater than said first diameter, said strap being stretchable when said end part is inserted into said aperture until said strap is situated adjacent said proximal portion, diameters, as used above, meaning the dimensions perpendicular to the pivot axis of the coupled parts.

* * * * *